United States Patent [19]

Draper et al.

[11] Patent Number: 5,595,978
[45] Date of Patent: *Jan. 21, 1997

[54] COMPOSITION AND METHOD FOR TREATMENT OF CMV RETINITES

[75] Inventors: Kenneth G. Draper, Boulder, Colo.; Sharon K. Chapman, Carlsbad; Daniel L. Kisner, Cardiff, both of Calif.

[73] Assignee: Isis Pharmaceuticals, Inc., Carlsbad, Calif.

[*] Notice: The term of this patent shall not extend beyond the expiration date of Pat. No. 5,442,049.

[21] Appl. No.: 233,711

[22] Filed: Apr. 26, 1994

Related U.S. Application Data

[63] Continuation-in-part of Ser. No. 568,366, Aug. 16, 1990, abandoned, Ser. No. 927,506, Nov. 19, 1992, and Ser. No. 9,263, Jan. 25, 1993, Pat. No. 5,442,049.

[30] Foreign Application Priority Data

Aug. 14, 1991 [WO] WIPO ............... PCT/US91/05815

[51] Int. Cl.$^6$ ............... A61K 48/00; C12Q 1/68; C07H 21/04
[52] U.S. Cl. ............... 514/44; 435/6; 435/91.1; 536/23.1; 536/24.5
[58] Field of Search ............... 435/91.1, 6; 514/44; 536/23.1, 24.5

[56] References Cited

U.S. PATENT DOCUMENTS 5,034,506  7/1994  Summerton et al. ............... 528/391

OTHER PUBLICATIONS

Azad et al. Anti Agents and Chemo Therp. Sep. 1993, vol. 37, pp. 1945–1954.
Stenberg et al. J. Vir. Dec. 1985, vol. 56 pp. 665–675.
Pam et al. Clin. Pharm. Aug 1990, vol. 9, pp. 613–631.
Uhlmann et al. Chem. Res. Jun. 1990, vol. 90, 544–579.
Stein et al. Science 261:1004 (1993).
Gennaro, Alfonso, Ed., Remington's Pharmaceutical Sciences, 18th Edition 1990. Mack Publishing Co., Easton, Pa.
P. E. Nielsen, M. Egholm, R. H. Berg, O. Buchardt, "Sequence–Selective Recognition of DNA by Strand Displacement with a Thymine–Substituted Polyamide", *Science* 1991, 254, 1497.
Flores–Aquiler et al. 7th Internal. Conf. on Antivir. Res. 23 (Suppl. 1) 1994 (89).

*Primary Examiner*—John L. Leguyader
*Attorney, Agent, or Firm*—Law Offices of Jane Massey Licata

[57] ABSTRACT

This invention concerns compositions and methods for the treatment of CMV infections. A composition including an antisense oligonucleotide targeted to the IE2 gene of CMV and a pharmaceutically acceptable carrier were used stop progression in CMV retinitis.

9 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:1:

GCGTTTGCTC TTCTTCTTGC G        2 1

COMPOSITION AND METHOD FOR TREATMENT OF CMV RETINITES

This application is a continuation in part of Ser. No. 07/568,366 filed Aug. 16, 1990 now abandoned; Ser. No. PCT/US91/05815 filed Aug. 14, 1991; Ser. No. 07/927,506 filed Nov. 19, 1992 pending; and Ser. No. 08/009,263 filed Jan. 25, 1993, now U.S. Pat. No. 5,442,049.

BACKGROUND OF THE INVENTION

Cytomegalovirus (CMV) is infectious to humans of all ages beginning with gestation. CMV infection causes a wide spectrum of diseases including severe congenital malformations, a mononucleosis syndrome in adolescent and young adults, and fatal disseminated infection in immunosuppressed patients. Since CMV is so common as a latent virus in the general population and since cell-mediated immunity is the important element in host defense for controlling its proliferation, it is not surprising that CMV is a major pathogen in immune-compromised patients. CMV is a major cause of dysfunction in a wide variety of organs in patients with AIDS. Many AIDS patients have persistent CMV viremia. Some patients are viremic at a time when they are asymptomatic or have mild constitutional symptoms, but also have Kaposi's sarcoma. Almost all are viremic when they have had other life-threatening opportunistic infections.

Cytomegalovirus retinitis is a severe problem in immunosuppressed patients and often leads to blindness. Immunosuppressed patients are also very susceptible to CMV pneumonitis, which is one of the most lethal of human viral diseases. Cytomegalovirus may also play a role in the progression of HIV infection to AIDS by stimulating the transcription of the HIV long terminal repeats (LTR) in nontransformed, co-infected T cells. Histologic examination of adrenals and brains from AIDS patients has suggested that the adrenalitis, encephalitis and peripheral neuropathy observed were caused by CMV infection.

CMV is considered to be an oncogenic virus. In vitro, CMV can transform cells and stimulate growth. Both human and non-human cells can undergo transformation when incubated with CMV. Transformed cells contain CMV antigens that are oncogenic when inoculated into appropriate animals. Moreover, oncogenic potential has been associated with specific segments of the CMV genome.

Human CMV is a large, enveloped herpesvirus whose genome consists of a double-stranded DNA molecule approximately 240,000 nucleotides in length. This genome is the most complex of all DNA viruses and is approximately 50% larger than the genome of herpes simplex virus (HSV). Intact viral DNA is composed of contiguous long (L) and short (S) segments, each of which contains regions of unique DNA sequence flanked by homologous regions of repetitive sequence. As a group, the human CMV isolates share at least 80% sequence homology, making it nearly impossible to classify cytomegaloviruses into subgroups or subtypes, although variations in the restriction endonuclease patterns of various CMV DNA preparations are identifiable in epidemiologically unrelated strains. The DNA of the prototypic strain of CMV (AD 169) has been sequenced and reported to contain a conservative estimate of 175 unique translational open reading frames (ORFs). A number of the predicted CMV gene products show homology to other human herpesvirus gene products.

In permissive human fibroblasts, CMV gene expression is regulated by a cascade of genetic events that act at both the transcriptional and translational levels. CMV gene expression can be divided into three phases which resemble those of HSV defined as the immediate early (IE), early and late periods. Following adsorption, penetration and uncoating of the virus, a group of viral transcripts, immediate early messenger RNAs (IE mRNAs) are synthesized within 1–4 hours even in the presence of translational inhibitors such as cycloheximide. In the normal course of infection, the IE mRNAs are translated and their protein products are instrumental in the onset of early transcriptional events. At least 4 proteins are synthesized from IE mRNAs, one of which is a glycoprotein. The IE1 and IE2 proteins are transcriptional activating factors for other CMV genes and the IE3 protein encompasses a region of the CMV genome which can transform NIH 3T3 cells in vitro. Early proteins are encoded by the mRNAs which are synthesized prior to viral DNA synthesis. A number of the early proteins play a role in nucleotide metabolism and DNA synthesis in the infected cell. After the onset of viral DNA synthesis, the transcription of the late mRNAs is maximal and probably reflects a template abundancy requirement similar to that observed for analogous HSV mRNAs. The late CMV proteins include the glycoprotein constituents of the viral envelope, the viral capsid proteins and other proteins which are necessary for assembly or structural integrity of the mature CMV particle and/or egress of the assembled virion from the infected cell. In addition to the transcriptional controls operant upon CMV gene expression, examples of post-transcriptional controls are known to influence the appearance of some CMV proteins. Splicing of mRNAs is more common than observed in HSV gene expression and the nucleotide sequence composition of the 5' nontranslated region in the cognate mRNA is reported to influence the synthesis of at least one early CMV protein.

Effective therapy for CMV has not yet been developed despite studies on a number of antiviral agents. Interferon, transfer factor, adenine arabinoside (Ara-A), acycloguanosine (Acyclovir, ACV) and certain combinations of these drugs have been ineffective in controlling CMV infections. Based on preclinical and clinical data, foscarnet (PFA) and ganciclovir (DHPG) show limited potential as antiviral agents. PFA treatment has resulted in the resolution of CMV retinitis in five AIDS patients to date. DHPG studies have shown efficacy against CMV retinitis and colitis. DHPG seems to be well tolerated by most treated individuals, but the appearance of a reversible neutropenia, the emergence of resistant strains of CMV upon long-term administration, and the lack of efficacy against CMV pneumonitis limit the long term applications of this compound. The development of more effective and less-toxic therapeutic compounds and methods is needed for both acute and chronic use.

Classical drug therapies have generally focused upon interactions with proteins in efforts to modulate their disease causing or disease potentiating functions. Such therapeutic approaches have failed for cytomegalovirus infections. The present invention is directed to an alternative approach to the treatment of such infections, the antisense inhibition of cytomegalovirus gene expression through the mediation of oligonucleotides.

SUMMARY OF THE INVENTION

This invention concerns compositions and methods for the treatment of CMV infections. A composition comprising an antisense oligonucleotide targeted to CMV IE2 and a pharmaceutically acceptable carrier are used to treat CMV infections, including CMV retinitis. A composition comprising the antisense oligonucleotide and a pharmaceutically acceptable carrier is administered either alone or in combination with a second anti-CMV or other antiviral agent.

DETAILED DESCRIPTION OF THE INVENTION

CMV is a major cause of dysfunction in a wide variety of organs in immunocompromised or immunosuppressed patients. Since CMV is so common as a latent virus in the general population and since cell-mediated immunity is the important element in host defense for controlling its proliferation, it is not surprising that CMV is a major pathogen in AIDS. Many AIDS patients have persistent CMV viremia and almost all are viremic after having had other life-threatening opportunistic infections. Diseases most clearly related to CMV infection in AIDS patients include gastrointestinal ulcerations, chorioretinitis and pneumonitis.

CMV retinitis is a devastating infection and rapid progression to blindness is not uncommon. It is characterized by progressively enlarging yellowish-white patches of retinal opacification, which are accompanied by retinal hemorrhages which usually begin adjacent to the major retinal vascular arcades. Patients are often asymptomatic until there is involvement of the fovea or optic nerve or until retinal detachment develops. Until the present invention, however, there has been no effective therapy for CMV infections in this setting.

Both currently used drugs i.e., ganciclovir, a nucleoside analog structurally related to acyclovir, (2-Amino-1,9 [[2-hydroxy-1-(hydroxymethyl)ethoxy]methyl]-6H-purin-6-one; 9-[(1,3-dihydroxy-2-propoxy) methyl]guanine;2'-nor-2'deoxyguanosine); and foscarnet (dihydroxyphosphinecarboxylic acid oxide trisodium salt; trisodium phosphonoformate; trisodium carboxyphosphate) are effective for only limited periods and progression of the infection occurs during maintenance therapy in many patients.

Ganciclovir has been shown to be useful in the management of CMV retinitis in patients with AIDS. Induction therapy is with 5 mg/kg twice a day for 10–14 days; maintenance therapy is 5 mg/kg daily. Unfortunately, progression of the disease is common even when maintenance therapy is administered. Systemic ganciclovir is most commonly administered intravenously. However, bone marrow suppression is a common side effect which is especially problematic if zidovudine (AZT) therapy is being undertaken simultaneously. Intravitreal ganciclovir has been used as an alternative. Systemic foscarnet, 60 mg/kg three times a day for 14 days followed by 90 mg/kg/day as maintenance therapy, has been found to improve patient survival as well as being effective against CMV retinitis, however, foscarnet is less well tolerated than systemic ganciclovir. Some patients develop intolerance to both foscarnet and ganciclovir, and others have CMV retinitis which is or becomes unresponsive to both drugs.

In the present invention, CMV retinitis is treated with a composition comprising an antisense oligonucleotide targeted to CMV IE2 and a pharmaceutically acceptable carrier. In the preferred embodiment the oligonucleotide comprises SEQ ID NO: 1 and the pharmaceutically acceptable carrier is a buffered solution (such as bicarbonate or phosphate). The composition is administered intravitreally in the preferred embodiment. The composition may also be administered in combination with a second anti-CMV agent such as ganciclovir or foscarnet. In the preferred embodiment, the antisense oligonucleotide composition is administered intravitreally and the second anti-CMV agent, intravenously. The antisense oligonucleotide ISIS 2922 (SEQ ID NO: 1), was evaluated for antiviral activity in combination with compounds currently used for treatment of human CMV or HIV infection. ISIS 2922 anti-human CMV activity was additive with that of ganciclovir (DHPG) or foscarnet, and was not adversely affected by AZT or ddC.

For CMV retinitis, the primary efficacy endpoints are the presence or absence of progression. Progression is defined as one of the following: appearance of any new lesions, 750 microns in diameter; advancement of the border of lesions existing at baseline, including satellite lesions, by 750 microns along a 750 micron front. The clinical impression of progression is confirmed by fundus photographs. Changes in border opacification of lesions present at baseline are also considered however an increase in border opacification is not interpreted as progression unless accompanied by at least one of the primary events defining progression.

A Phase I study of ISIS 2922 (SEQ ID NO:1) in ten patients with CMV retinitis has been conducted. These patients were HIV positive patients having a clinical diagnosis of CMV retinitis in one or both eyes. The patients had all progressed at least once on maintenance therapy with ganciclovir or foscarnet after initially responding to an induction regimen of either ganciclovir or foscarnet and could no longer be effectively treated with these therapeutic agents.

Three doses (75 µg, 150 µg, and 300 µg) were selected to provide intravitreal composition concentrations of approximately 2 µM, 4 µM and 8 µM, respectively. The dose regimen, selected on the basis of animal pharmacokinetic studies, was weekly doses followed by an every-other-week maintenance schedule. Lesion status was followed by routine clinical ophthalmic examinations and fundus photography. Ten patients were treated in this study and seven continue to receive treatment. A summary of each of these ten patients is presented below.

Patient #01-001 75 µg (2 µM) Dosing Regimen

This 48 year-old male was diagnosed with CMV retinitis 11 months prior to study entry. He was initially given i.v. ganciclovir and progressed in 21 weeks. The patient was reinduced on two subsequent occasions with i.v. ganciclovir and progressed, each time, within 6 weeks. He was then treated with i.v. foscarnet but developed toxicity within the first month. Prior to entering the study, the patient was receiving a combination of i.v. ganciclovir and intravitreal foscarnet. He started by receiving foscarnet injections twice a week. When the regimen was changed to once a week, he progressed and returned to the twice a week regimen. He had received 5 foscarnet injections in the third month before entering the study and 7 injections in the second month before entering the study. He had a $CD_4$ count of 4 on study entry and his baseline ocular status indicated inflammation and uveitis in the left and right eyes. The patient received 2 weekly doses of 75 µg ISIS 2922 in the right eye without complications or adverse events but he was shown to have progressed at the time he returned for his third dose (2 weeks on study). His visual acuity was unchanged from baseline. He was discontinued from the study to receive twice a week intravitreal foscarnet.

Patient #01-002 75 µg (2 µM) Dosing Regimen

This 34 year-old male was diagnosed with CMV retinitis 21 months prior to study entry. He received i.v. ganciclovir and i.v. IG and remained free of progression for 39 weeks. Since that time, he was reinduced on two subsequent occasions with i.v. ganciclovir and progression again occurred within 8 and 4 weeks, respectively. Three months before study entry, he received i.v. foscarnet but he did not have a complete remission and his retinitis continued to progress. He had a $CD_4$ count of 4 on study entry and his baseline ocular status indicated inflammation and uveitis in the left eye. The patient received 2 weekly doses of 75 μg ISIS 2922 in the left eye but was shown to have increased inflammation with possible lesion progression at the time of his third dose (2 weeks on study). His vision was unchanged from baseline. The inflammation was suspected to be endophthalmitis so a vitrectomy was performed and the patient was discontinued from the study. The cytology findings reported proteinaceous debris, scattered lymphs and neutrophils, but the bacteriology cultures were negative.

Patient #01-003 150 μg (4 μM) Dose Regimen

This 32 year-old male was diagnosed with CMV retinitis in April 1993 (7 months prior to study entry). He received i.v. foscarnet for approximately 2 months until he progressed and experienced nausea and vomiting believed to be associated with foscarnet. He then received i.v. ganciclovir which did not lead to remission and his retinitis continued to smolder. He had a $CD_4$ count of 2 on study entry with inflammation and uveitis in his left eye. After receiving his second and third weekly doses of ISIS 2922, positive ophthalmic changes were observed which were confirmed by fundus photography. There was a marked decrease in lesion border opacification without lesion advancement. A mild vitreous hemorrhage was observed after 2 weeks on study and resolved without intervention. In general, ISIS 2922 has been well tolerated by this patient. Reports of mild or moderate pain have been received on 2 occasions for a duration of 2 days in both cases. The causes were recorded as unknown. The patient continues to receive ISIS 2922 on an every-other-week maintenance schedule. To date, the patient has received 9 doses of ISIS 2922 over a period of 16 weeks without evidence of lesion progression.

Patient #01-004 150 μg (4 μM) Dose Regimen

This 40 year-old male was diagnosed with CMV retinitis 26 months prior to study entry. He received i.v. ganciclovir for approximately 24 months. He experienced 3 relapses and he continued to progress in spite of extended induction dosing. He was switched to i.v. foscarnet but developed renal toxicity. He had a $CD_4$ count of 3 on study entry. The patient received 2 doses of 150 μg ISIS 2922 and continued to progress. He complained of single occurrences of pain, watery eye and photophobia as well as a moderate increase in inflammation when he returned for his third dose. His vision was unchanged from baseline. The patient did not require treatment for the ocular events or for the inflammation but he was removed from the study due to progression. The ocular events were resolved and he refused further treatment for his retinitis.

Patient #02-001 150 μg (4 μM) Dose Regimen

This 26 year-old male was diagnosed with CMV retinitis 4 months prior to study entry. He was treated for 10 weeks with i.v. ganciclovir during which time the retinitis continued to smolder in the right eye and the left eye became active. Ganciclovir was discontinued and he was given 4 weeks of i.v. foscarnet during which time the progression in the left eye was under control but the right eye continued to show progression until light perception was lost. The patient was discontinued from foscarnet due to intolerance. A week later he received his first intravitreal injection of ISIS 2922 in the left eye. At study entry, the patient's $CD_4$ count was 35 and the initial ocular exam revealed inflammation and uveitis in both eyes and vitreal opacification in the right untreated eye. The patient has been on the ISIS 2922 clinical study for 9 weeks. He has reported transient local ocular effects in the treated eye including mild to moderate ocular pain, subconjunctival hemorrhage and cloudy vision along with a moderate case of vitritis and vitreal opacification. All of these events have resolved or are resolving without dose interruption. A positive clinical response was confirmed by fundus photography within the first three weeks of the study but the investigator had already elected to increase the dose to 300 μg (8 μM vitreal concentration) every two weeks for maintenance to provide the best opportunity for a clinical response in this patient who has only one functional eye. To date, the patient has received 7 doses of ISIS 2922 (4×150 μg and 3×300 μg) over a 9-week period and the CMV retinitis activity continues to show improvement without evidence of progression.

Patient #01-005 300 μg (8 μM) Dose Regimen

This 37 year-old male was diagnosed with CMV retinitis in his right eye 8 weeks prior to study entry. This was the first opportunistic infection experienced by this patient since he was diagnosed HIV positive 4 years previously. He was treated for 4 weeks with i.v. ganciclovir but the lesion remained active and smoldering. The patient refused therapy with foscarnet and was entered into the ISIS 2922 clinical study to receive the 300 μg dosing regimen in the right eye. He had a $CD_4$ count of 10 at study entry and his baseline ocular exam revealed inflammation and uveitis in the right eye and posterior subcapsular cataracts in both eyes. To date, the patient has received 6 doses of ISIS 2922 over an 8-week period. Following the 2nd, 3rd and 4th doses, the patient experienced intermittent blurred vision with temporary decreases in color perception but the events were temporary and have not required intervention. A positive clinical response was noted within the first 4 weeks and the lesion continues to be quiet without evidence of progression.

Patient #01-006 300 μg (8 μM) Dose Regimen

This 37 year-old female was diagnosed with CMV retinitis in the right eye 11 months prior to study entry. The patient received multiple courses of ganciclovir and foscarnet. The disease spread to the left eye but not before the right eye had advanced resulting in a retinal detachment. The patient entered the ISIS 2922 trial for treatment to the left eye. She had a $CD_4$ count of 0 at study entry and the baseline ocular exam revealed a constant blurred vision and floaters for the left eye. The patient has received 6 doses over a 7-week period. Positive changes were observed on fundus photography within the first 3 weeks on study and the patient's treated eye (left eye) continues to improve without lesion advancement. On examination at Week 5, the lesion in the patient's right eye appeared active and progressing. The decision was reached to treat the right eye with i.v. ganciclovir in combination with the ongoing intravitreal therapy of the left eye with ISIS 2922.

Patient #03-001 300 μg (8 μM) Dose Regimen

This 34 year-old male was diagnosed with CMV retinitis 1 year before study entry. Although the number of treatment courses and relapses have not been documented, the patient had received ganciclovir and foscarnet and both treatments were discontinued due to toxicities including myelosuppression and renal toxicity, respectively. Both eyes are affected with CMV retinitis. There is no light perception in the right eye and the decision was reached to treat the left eye in the ISIS 2922 clinical trial. Ocular examinations at baseline indicate that the left eye had intermittent blurred vision, decreased peripheral vision, optic disc atrophy and uveitis. To date, this patient has received 4 doses of ISIS 2922 over a period of 3 weeks. The drug has been well tolerated. The only ocular event reported has been a mild macula edema at three weeks. After 3 weeks on study and 4 doses, ophthalmic examinations have revealed decreases in CMV retinitis activity and lesion border opacification. Retinal photographs have been taken on a regular basis and results should be available soon.

Patient #01-007 300 μg (8 μM) Dose Regimen

This 43 year-old male was diagnosed with CMV retinitis 8 months before study entry. The patient has failed both ganciclovir and foscarnet. Both eyes are being treated with ISIS 2922. The patient has been on study for 2 weeks with no reported adverse events.

Patient #03-002 300 μg (8 μM) Dose Regimen

This 33 year-old male was diagnosed with CMV retinitis 19 months before study entry. Although the number of prior treatment courses and relapses have not been documented, the patient had smoldering retinitis at study entry and was reported to be intolerant to both ganciclovir and foscarnet. He has been on the study for 1 week.

For five out of these ten patients who had experienced progressions on ganciclovir or foscarnet, treatment with a composition of the present invention effectively halted disease progression. In one patient infected in both eyes, intravitreal treatment with the composition of the invention succeeded where ganciclovir therapy alone had failed. Spontaneous disease regression or improvement in this patient population is not expected.

In the present invention a method is provided for the treatment of an animal, preferably a human, having a CMV infection which comprises administering an effective amount of a composition comprising an antisense oligonucleotide targeted to IE2 and a pharmaceutically acceptable carrier, either alone or in combination with a second anti-CMV agent or composition such as ganciclovir or foscarnet, or other antiviral agent or composition. By "animal" it is meant to include, but is not limited to, mammals, fish, amphibians, reptiles, birds, marsupials, and most preferably, humans. An "effective amount" refers to a concentration of an oligonucleotide routinely determined by one of skill in the art in accordance with the teachings of the present invention which is capable of treating a CMV infection. The composition of the invention may be administered intravitreally or intravenously. In the treatment of CMV retinitis, intravitreal administration is preferred. In the embodiment of the invention wherein a second anti-CMV agent of composition is administered, it is preferred that the administration be intravenous. In another embodiment, an effective amount of a composition comprising an antisense oligonucleotide targeted to IE2 and a pharmaceutically acceptable carrier, is administered in combination with an antiviral agent such as AZT or acyclovir.

Pharmaceutically acceptable carriers include, but are not limited to saline solutions and buffered solutions. Suitable pharmaceutically acceptable carriers are well known in the art and are described for example in Gennaro, Alfonso, Ed., Remington's Pharmaceutical Sciences, 18th Edition 1990. Mack Publishing Co., Easton, Pa., a standard reference text in this field. Pharmaceutical carriers may be selected in accordance with the intended route of administration and the standard pharmaceutical practice. For example, for intravitreal injection it is preferred that the oligonucleotide be administered in a buffered solution, preferably bicarbonate buffer. For intravenous administration, a saline solution is preferred.

An oligonucleotide in accordance with the invention preferably has SEQ ID NO: 1 or an effective portion thereof or is targeted to a similar IE2 target. ISIS 2922 is targeted to the CMV IE2. The IE2 protein is capable of transcriptionally activating many of the HCMV early and late genes in a manner similar to other known transactivating proteins of cellular and viral origin. Thus, the IE2 protein is believed to be one of the master switches for HCMV gene expression. It is preferred to employ any of these oligonucleotides (or their analogs) or any of the similar oligonucleotides which persons of ordinary skill in the art can prepare from knowledge of the preferred antisense target for the modulation of the CMV infection. It is to be expected that differences in the DNA of cytomegalovirus from different species and from different types within a species exist. Thus, it is believed, for example, that the regions of the various cytomegalovirus species serve essentially the same function for the respective species and that interference with expression of the genetic information will afford similar results in the various species. This is believed to be so even though differences in the nucleotide sequences among the species doubtlessly exist. Accordingly, nucleotide sequences set forth in the present specification will be understood to be representational for the particular species being described. Homologous or analogous sequences for different species of cytomegalovirus are specifically contemplated as being within the scope of this invention.

The oligonucleotides and analogs used in accordance with this invention may be conveniently and routinely made through the well-known technique of solid phase synthesis. Equipment for such synthesis is sold by several vendors including Applied Biosystems. Any other means for such synthesis may also be employed, however, the actual synthesis of the oligonucleotides are well within the talents of the routineer. It is also well known to use similar techniques to prepare oligonucleotide analogs such as the phosphorothioates and alkylated derivatives.

In accordance with the present invention, oligonucleotides having a sequence of nucleotide bases specifically hybridizable with a selected sequence of a cytomegalovirus DNA or RNA are provided. "Hybridization," in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them. The term "specifically hybridizable" refers to a sufficient degree of complementarity such that stable and specific binding occurs between the target and the oligonucleotide or analog. It is understood that an oligonucleotide need not be 100% complementary to its target nucleic acid sequence to be specifically hybridizable. An oligonucleotide is specifically hybridizable when binding of the oligonucleotide to the target interferes with the normal function of the messenger RNA to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted. It has been determined that targeting cytomegalovirus DNA or RNA coding for IE2 is a key to the effective antisense therapy with these oligonucleotides. This relationship between an oligonucleotide and its complementary target is commonly denoted as "antisense." The oligonucleotides are able to inhibit the function of RNA; either its translation into protein, its translocation into the cytoplasm, maturation, or any other activity necessary to its overall biological function. The failure of the RNA to perform all or part of its function results in failure of a portion of the genome controlling the normal life cycle of the virus.

It has now been found that oligonucleotides can be designed which are effective in diminishing CMV infection. It is preferred that oligonucleotides have between about 5 and about 50 nucleic acid base units. It is preferred that the oligonucleotide be specifically hybridizable with at least a portion of DNA or RNA coding for the IE2 protein. The oligonucleotide may be modified to reduce nuclease resistance and to increase efficacy.

In the context of this invention, the term "oligonucleotide" refers to an oligomer or polymer of ribonucleic acid or deoxyribonucleic acid. This term includes oligomers consisting of naturally occurring bases, sugars and intersugar (backbone) linkages as well as oligomers having non-naturally occurring portions which function similarly. Such modified or substituted oligonucleotides are often preferred over native forms because of properties such as, for example, enhanced cellular uptake, increased target affinity and/or increased stability in the presence of nucleases.

Specific examples of some preferred oligonucleotides envisioned for this invention may contain phosphorothioates, phosphotriesters, methyl phosphonates, short chain alkyl or cycloalkyl intersugar linkages or short chain heteroatomic or heterocyclic intersugar linkages. Most preferred are those with $CH_2$—$NH$—$O$—$CH_2$, $CH_2$—$N(CH_3)$—$O$—$CH_2$, $CH_2$—$O$—$N(CH_3)$—$CH_2$, $CH_2$—$N(CH_3)$—$N(CH_3)CH_2$ and $O$—$N(CH_3)$—$CH_2$—$CH_2$ backbones (where phosphodiester is $O$—$P$—$O$—$CH_2$). Also preferred are oligonucleotides having morpholino backbone structures. Summerton, J. E. and Weller, D. D., U.S. Pat. No. 5,034,506. In other preferred embodiments, such as the protein-nucleic acid (PNA) backbone, the phosphodiester backbone of the oligonucleotide may be replaced with a polyamide backbone, the bases being bound directly or indirectly to the aza nitrogen atoms of the polyamide backbone. P. E. Nielsen, M. Egholm, R. H. Berg, O. Buchardt, Science 1991, 254, 1497. Other preferred oligonucleotides may contain alkyl and halogen-substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. Oligonucleotides may also have sugar mimetics such as cyclobutyls in place of the pentofuranosyl group. Modified bases or "universal" bases and nucleotides such as hypoxanthine and inosine may also be incorporated.

An animal having a cytomegalovirus infection is treated by administering an oligonucleotide in accordance with this invention. Persons of ordinary skill can easily determine optimum dosages, dosing methodologies and repetition rates in accordance with the weight and condition of the animal. Such treatment is generally continued until either a cure is effected or a diminution in the disease state is achieved.

The invention is further illustrated by the following non-limiting examples.

EXAMPLES

Example 1

Synthesis and Characterization of Oligonucleotides

Oligonucleotides were synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2M solution of 3H-1,2-benzodithiole-3-one 1,1-dioxide in acetonitrile for the stepwise thiation of the phosphite linkages. The thiation cycle wait step was increased to 68 seconds and was followed by the capping step. 2'-O-methyl phosphorothioate oligonucleotides were synthesized using 2'-O-methyl β-cyanoethyldiisopropyl-phosphoramidites (Chemgenes, Needham Mass.) and the standard cycle for unmodified oligonucleotides, except the wait step after pulse delivery of tetrazole and base was increased to 360 seconds. The 3'-base used to start the synthesis was a 2'-deoxyribonucleotide. 2'-O-propyl phosphorothioate oligonucleotides were prepared as disclosed in U.S. patent application Ser. No. 566,977, filed Aug. 13, 1990, which is assigned to the same assignee as the instant application and which is incorporated by reference herein. 2'-fluoro phosphorothioate oligonucleotides were synthesized using 5'-dimethoxytrityl-3'-phosphoramidites and prepared as disclosed in U.S. patent application Ser. No. 463,358, filed Jan. 11, 1990, and 566,977, filed Aug. 13, 1990, which are assigned to the same assignee as the instant application and which are incorporated by reference herein. The 2'-fluoro oligonucleotides were prepared using phosphoramidite chemistry and a slight modification of the standard DNA synthesis protocol: deprotection was effected using methanolic ammonia at room temperature.

After cleavage from the controlled pore glass column (Applied Biosystems) and deblocking in concentrated ammonium hydroxide at 55° C. for 18 hours, the oligonucleotides were purified by precipitation twice out of 0.5 M NaCl with 2.5 volumes ethanol. Analytical gel electrophoresis was accomplished in 20% acrylamide, 8M urea, 45 mM Tris-borate buffer, pH 7.0. Oligodeoxynucleotides and phosphorothioate oligonucleotides were judged from electrophoresis to be greater than 80% full length material.

Example 2

ELISA assay for inhibition of CMV replication by antisense oligonucleotides

Oligonucleotides complementary to human cytomegalovirus mRNA were tested for antiviral activity in an ELISA-based assay of CMV replication. Normal human dermal fibroblasts (Clonetics Corp., San Diego, Calif.) were grown in serum-free medium (Clonetics) and used to seed 96-well plates. When cells are approximately 80% confluent, they are pretreated with oligonucleotides. Approximately 20 hours after pretreatment, the medium (containing oligonucleotides) is carefully poured off and the cells are washed twice with warmed fibroblast basal medium (FBM, Clonetics). Cells are then infected with 100 μl per well of CMV stock diluted in FBM. The plates are incubated at 37° C. for two hours. The medium (containing virus) is then carefully poured off and replaced with fresh, prewarmed FBM medium, 100 μl per well. The plates are briefly incubated at 37° C. and then 5 μl of oligonucleotide, diluted in FBM, are reintroduced into the medium in each well. Two days later, cells are post-treated again with oligonucleotides in the same way. On day six, the plates are prepared for ELISA.

In preparation for ELISA, the medium is carefully poured off the plates, and cells are fixed in 200 μl of absolute ethanol per well. Cells are fixed for 30 minutes at room temperature, the ethanol is then removed and plates are air-dried. Plates are blocked for one hour prior to ELISA with PBS containing 2% BSA. Blocking solution is removed and 100 μl of an anti-CMV antibody, diluted 1:2000 in PBS with 1% BSA, is added. Cells are incubated in antibody for one hour at 37° C. and washed three times in PBS. The secondary antibody, biotinylated goat anti-mouse IgG (Bethesda Research Labs, Md.), is diluted 1:1000 in PBS with 1% BSA, and incubated with cells for one hour at 37° C. Cells are then washed and incubated for one hour at 37° C. in streptavidin-B-D-galactosidase. Color is developed with chlorophenol red-B-D-galactopyranoside, 20 mg dissolved in 10 ml of 50 mM Na Phosphate, 1.5 mM MgCl2; plates are shaken for 10 minutes and the absorbance is read at 575 nm.

ISIS 2922, an oligonucleotide complementary to human CMV was tested for antiviral activity.

At a screening concentration of 5 μM this oligonucleotide demonstrated greater than 90% inhibition of virus. Dose-response experiments differentiated between non-specific effects and sequence-specific inhibition of CMV replication by this oligonucleotide. Compound ISIS 2922 showed inhibition of CMV replication at lower doses than randomized oligonucleotides with no complementarity to CMV. The activity of ISIS 2922 relative to a randomized control oligonucleotide was confirmed in an independent dose-response experiment.

Example 3

Comparison of ISIS 2922 to ganciclovir (DHPG)

The antiviral activity of oligonucleotide 2922 was compared to the antiviral activity of ganciclovir in dose-response experiments using the ELISA assay described in Example 2, with either ganciclovir or oligonucleotide being added after infection with virus. The oligonucleotide demonstrated potent antiviral activity, with $EC_{50}$s (50% effective concentration, the concentration needed to give 50% inhibition) against the AD 169 strain of human CMV of 0.1 μM for ISIS 2922. The $EC_{50}$ for ganciclovir in this experiment was 3 μM, demonstrating that ISIS 2922 was approximately 30 fold more potent than ganciclovir on a molar basis.

Similar results were obtained when the antiviral activity of 2922 and ganciclovir was determined for the Towne strain of human CMV.

Example 4

Plaque reduction assay

Six-well culture plates were seeded with NHDF cells at a density of 500,000 cells per well in serum-free FGM. Subconfluent monolayers were pretreated with oligonucleotides overnight, and then rinsed three times to remove residual oligonucleotide prior to virus infection. Human CMV in FGM was added to cells at a dilution sufficient to result in the formation of approximately 100 plaques per well in untreated cells. After a two-hour adsorption, virus was removed and cells were overlaid with a 1:1 mixture of 1% Seaplaque agarose (FMC) and 2X minimal essential medium. Duplicate samples were counted and the mean expressed as the percent of plaques which developed in untreated cells.

Treatment of host cells with ISIS 2922 reduced the ability of human CMV to form plaques on monolayers of NHDF cells. At a concentration of 1 μM plaque formation was inhibited by greater than 99%.

Example 5

Yield reduction assay

Six-well culture plates were seeded with NHDF cells at a density of 500,000 cells per well in serum-free FGM or FGM containing 0.2% FBS. Subconfluent monolayers were pretreated with oligonucleotides overnight. After rinsing cells three times to remove residual oligonucleotide, virus in FGM was added and allowed to adsorb for two hours. Virus was then removed and cells were overlaid with fresh medium containing oligonucleotide. For evaluation of total virus yield, infected cells were incubated for 8 days, scraped into the culture supernatant and stored frozen at −80° C.

Infectious virus yield from harvested samples was determined in duplicate by standard plaque assay on monolayers of NHDF cells. An agarose overlay consisting of a 1:1 mixture of 1% Seaplaque agarose (FMC) and 2X minimal essential medium was applied to cells after adsorption. Following incubation for 8 days, cells were fixed in formaldehyde and stained overnight with methylene blue in phosphate buffered saline.

The ability of ISIS 2922 to inhibit production of infectious human CMV in NHDF cells was determined using the yield reduction assay. 90% and 99% inhibition of infectious virus production was achieved at 1.2 μM and 2.2 μM concentrations of ISIS 2922, respectively, when evaluating combined extracellular and intracellular virus yield. In contrast, 90% and 99% inhibition of CMV production by ganciclovir was only achieved at concentrations of 16 μM and 36 μM, respectively. A control oligonucleotide showed no inhibition of infectious CMV yield at doses up to 3 μM.

Example 6

Reduced expression of human CMV immediate early proteins in ISIS 2922-treated cells The steady-state levels of immediate early proteins in CMV-infected NHDF cells were examined using Western blot analysis. Subconfluent monolayers of NHDF cells in six-well culture plates were treated with oligonucleotide and infected as described above. Forty-eight hours after infection, medium was aspirated and cells were scraped into 200 μl of lysis buffer (20 mM Tris-HCl, pH 7.5; 20 mM KCl; 5 mM EDTA; 1% Triton X-100; 0.1 mM leupeptin; 10 μg/ml aprotinin). After pelleting nuclei and debris (15,000 xg for 10 minutes), the supernatant was transferred to a fresh tube, and protein from a 10 μl sample was fractionated by electrophoresis on a denaturing sodium dodecyl sulfate, 8% polyacrylamide gel under reducing conditions. Fractionated proteins were transferred electrophoretically to nitrocellulose membranes and IE2 polypeptides were detected using a mouse monoclonal antibody (MAB810, Chemicon, Temecula, Calif.) which recognizes a shared epitope on both IE1 and IE2 proteins. Alkaline phosphatase-conjugated goat anti-mouse IgG was used as a secondary antibody, and blots were developed in NBT and BCIP (BRL Gibco, Gaithersburg, Md.).

The levels of both immediate early polypeptides were reduced in CMV-infected cells treated with ISIS 2922. Both proteins were significantly reduced after treatment with 0.3 μM oligonucleotide, and were undetectable in cells treated with 1 μM oligonucleotide.

The ability of ISIS 2922 to inhibit expression of immediate early proteins was confirmed qualitatively using immunofluorescent staining of human CMV-infected cells. Subconfluent NHDF cells in wells of a four-chamber culture slide (Costar) were pretreated with oligonucleotide overnight (15–20 hours), infected with human CMV using a M.O.I. of 3 pfu/cell, treated for an additional 24 hours at 37° C., and fixed in ethanol at −20° C. Immediate early proteins were detected using the same monoclonal antibody, MAB810, used for Western blot analysis, and rhodamine-conjugated goat anti-mouse IgG. Cells were examined and photographed using a Nikon epifluorescence microscope.

After treatment with ISIS 2922 at a concentration of 1 µM, the number of cells exhibiting the nuclear immunofluorescence characteristic of human CMV-infected cells 24 hours after infection was reduced to less than 10%, compared to over 70% for control cells not treated with oligonucleotide. The intensity of fluorescence was also reduced in oligonucleotide-treated cells.

Example 7

ISIS 2922 can be used in combination with other antiviral drugs

ISIS 2922 was evaluated for antiviral activity in combination with compounds currently used for treatment of human CMV or HIV infection. ISIS 2922 anti-human CMV activity was additive with that of ganciclovir (DHPG) or foscarnet, and was not adversely affected by AZT or ddC.

composition comprising SEQ ID NO: 1 and a pharmaceutically acceptable carrier to an animal having CMV retinitis.

2. The method of claim 1 wherein the pharmaceutically acceptable carrier is a buffered solution.

3. The method of claim 1 wherein the animal is a human.

4. A composition comprising SEQ ID NO: 1 and a pharmaceutically acceptable carrier.

5. A composition comprising SEQ ID NO: 1 and a bicarbonate buffered solution.

6. A method for the treatment of CMV retinitis comprising administering an effective amount of a composition of claim 4 intravitreally in combination with ganciclovir to an animal having CMV retinitis.

7. A method for the treatment of CMV retinitis comprising administering an effective amount of a composition of claim 5 intravitreally in combination with ganciclovir to an animal having CMV retinitis.

8. A method for the treatment of CMV retinitis comprising administering an effective amount of a composition of claim 4 intravitreally in combination with foscarnet to an animal having CMV retinitis.

9. A method for the treatment of CMV retinitis comprising administering an effective amount of a composition of claim

What is claimed:

1. A method for treating CMV retinitis comprising administering by intravitreal injection an effective amount of a 5 intravitreally in combination with foscarnet to an animal having CMV retinitis.

* * * * *

UNITED STATES PATENT AND TRADEMARK OFFICE
CERTIFICATE OF CORRECTION

PATENT NO. : 5,595,978
DATED : January 21, 1997
INVENTOR(S) : Draper, et. al.

It is certified that error appears in the above-indentified patent and that said Letters Patent is hereby corrected as shown below:

Title page, item [54] and col. 1, line 2 delete "RETINITES" and insert-- RETINITIS--.

Signed and Sealed this

Twenty-ninth Day of July, 1997

Attest:

BRUCE LEHMAN

*Attesting Officer*              *Commissioner of Patents and Trademarks*